United States Patent [19]

Fischer

[11] Plant 5,193

[45] Feb. 21, 1984

[54] AFRICAN VIOLET PLANT

[75] Inventor: Arnold Fischer, Hanover, Fed. Rep. of Germany

[73] Assignee: Pan American Plant Company, Parrish, Fla.

[21] Appl. No.: 390,799

[22] Filed: Jun. 21, 1982

[51] Int. Cl.[3] ..... A01H 5/00

[52] U.S. Cl. ..... Plt./69

[58] Field of Search ..... Plt./69

*Primary Examiner*—Robert E. Bagwill

*Attorney, Agent, or Firm*—Schwartz, Jeffery, Schwaab, Mack, Blumenthal & Koch

[57] ABSTRACT

A vigorous and profusely flowering African violet known by the cultivar name Fairy Princess and having flowers which range in color from essentially solid purple to essentially entirely white and ranges of variegation therebetween, with the flowers being carried on erect peduncles to form a massive bouquet above the foliage.

5 Drawing Figures

1

The present invention comprises a new and distinct cultivar of African violet plant, botanically known as Saintpaulia hybrids, and hereinafter referred to by the cultivar name Fairy Princess.

The new cultivar was referred to during the breeding and selection process by the designation V7-C105-N, and is the product of a planned breeding program. The basic objective of the breeding program was to create a new African violet cultivar having a profusion of blooms varying from essentially solid purple or white to variegated combinations of these colors. The resulting cultivar is very unique, and in certain instances each bloom on the plant will be distinct with regard to color relative to the other blooms.

The new cultivar was originated from a cross made in a controlled breeding program in Hanover, West Germany. The female and male parents are unknown at this time.

Fairy Princess was discovered and selected by me as a flowering plant within the progeny of the stated cross in a controlled environment in Fallbrook, Calif. Asexual reproduction of the new cultivar by leaf cuttings, as initially performed by me at Fallbrook, Calif., and subsequently in Chicago, Ill., and Parrish, Fla., have demonstrated the combination of characteristics as herein disclosed for the new cultivar are firmly fixed and are retained through successive generations of asexual reproduction.

Fairy Princess has not been observed under all possible environmental conditions. The phenotype may vary significantly with variations in environment such as temperature, light intensity and day length. The following observations, measurements and values describe the new cultivar as grown under greenhouse conditions which closely approximate those used in commercial practice.

The following traits have been repeatedly observed and are determined to be basic characteristics of Fairy Princess, which in combination distinguish this African violet as a new and distinct cultivar:

1. The foremost characteristic is the variance of flower color. Within a single plant, the flowers may vary from completely white to completely purple and ranges of variegation therebetween. The cultivar blooms profusely and intermittently year round, and in subsequent flowerings the same flower colors reappear, thereby rendering the cultivar stable.

2

2. The flowers are held on erect peduncles above the foliage to form a massive colorful bouquet.

3. Abundant green foliage, with the margins being wavy to repand.

4. Vigorous growth habit.

The accompanying photographic drawings show typical specimen plants of the new cultivar. The colors appearing in the photographs are as true as possible for color illustrations of this type. The photograph at the top of Sheet 1 illustrates (at the left) blooms which are essentially purple, and blooms which are variegated, although predominately purple. The photograph at the bottom of Sheet 1 illustrates a bouquet in which a majority of the blooms are essentially entirely white, or white with purple centers and edges, with this photograph also showing other ranges of variegation. At the top of Sheet 2 a bouquet is illustrated which includes both essentially entirely white or entirely purple flowers, and ranges of variegation. At the bottom of Sheet 2 there are illustrated 5 individual flowers to either side of which are R.H.S. Colour Chart inserts so that the purple flower color as specified in the color values set forth hereinbelow can be readily seen. Sheet 3 comprises a black and white illustration showing bottom views of several foliage leaves.

In the following description, color references are made to the Royal Horticultural Society Colour Chart (R.H.S.), except where general colors of ordinary significance are referred to.

Botanical classification: Saintpaulia hybrids, cv. Fairy Princess.

Parentage:

*Male parent.*—Unknown.

*Female parent.*—Unknown.

Propagation: The new cultivar holds its distinguishing characteristics through successive propagations by leaf cuttings.

Plant: Generally rosette in shape, from 7 cm. to 11 cm. in height when fully grown, growth rate vigorous.

Leaves:

*General form.*—Oval with broadly acute apex and cordate base, abundant in quantity.

*Diameter.*—4×5 cm. to 7×8 cm.

*Texture.*—Glossy.

*Veins.*—Pinnate.

*Color* (*upperside*).—147A. (Underside): 147D.

*Petiole.*—4–10 cm. in length.

Flowers:

*Buds.*—Up to 1 cm. in diameter and length, round in form, with normal rate of opening; color when sepals first divide, 147D; color when petals begin to unfurl, approximately 155D.

*Sepals.*—Five in number, lanceolate in shape, branched; when flowers open, sepals stand up; color inside and outside 147C.

*Phyllaries.*—Two in number, lanceolate in shape, color 147B.

*Peduncle.*—1–3 cm. in length, slender, erect, color 147D, upright and normal in strength, color 147D.

Individual flowers:

*Size.*—Medium size, ranging from 2.5–3.5 cm. in diameter, and 1 cm. in depth.

*Color (upperside).*—Ranging from 80A–C to white 155D, and ranges of variegation therebetween; near 80A in center. (Underside): Generally as above.

*Borne.*—Cymose clusters formed on upright peduncles 4–7 cm. in length; generally cup-shaped when bloom first opens, becoming generally flat; 5–8 petals per bloom, with the petals being sympetalous.

*Shape.*—Single zygomorphic rotate, margin ruffled, apex rounded.

*Flowering habit.*—Flowers profusely and intermittently year round, with blooms lasting 2–3 weeks after which the petals dry up and turn brown but do not drop.

Reproductive organs:

*Stamens.*—2–3 in number, borne singly on one side of ovary, anthers basifixed. Anthers: 2 mm.×2 mm. in size, yellow in color. Filaments: 2–3 mm. in length.

*Pistils.*—One in number. Styles: 3–4 mm. in length, color 80C. Ovaries: Superior.

Disease resistance: No diseases noted to date.

General observations:

*Fairy Princess.*—Is a very unique variety in that the flower color from plant to plant will vary from a dominant purple wherein certain flowers are entirely that color, to a dominant white, and to all ranges of variegation therebetween. The overall effect is very interesting. The single flowers appear well above the foliage and provide a pleasant contrast therewith. The plant may be finished in 10–12 weeks from a 2¼″ plant in a controlled environment.

I claim:

1. A new and distinct cultivar of African violet known by the cultivar name Fairy Princess, and described and illustrated, and particularly characterized by its profuse flowering and vigorous growth habit, with the flowers being held above the foliage on erect peduncles to form a massive colorful bouquet, its flowers which range in color from essentially entirely purple to entirely white, and all ranges of variegation of these colors.

* * * * *

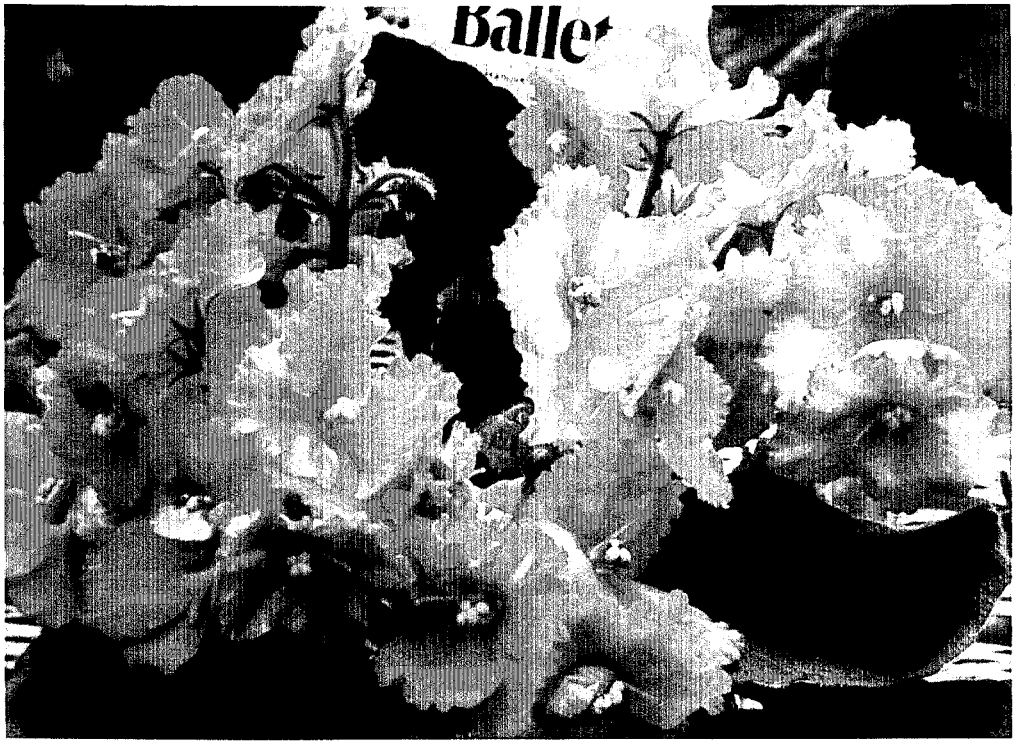
Ballet
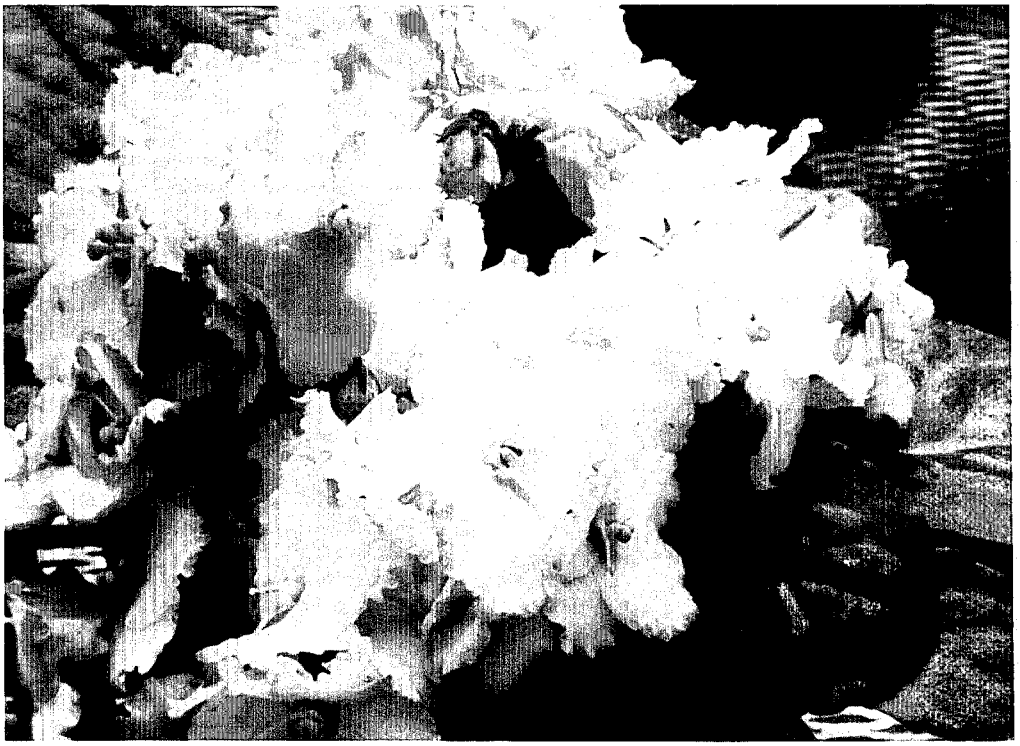

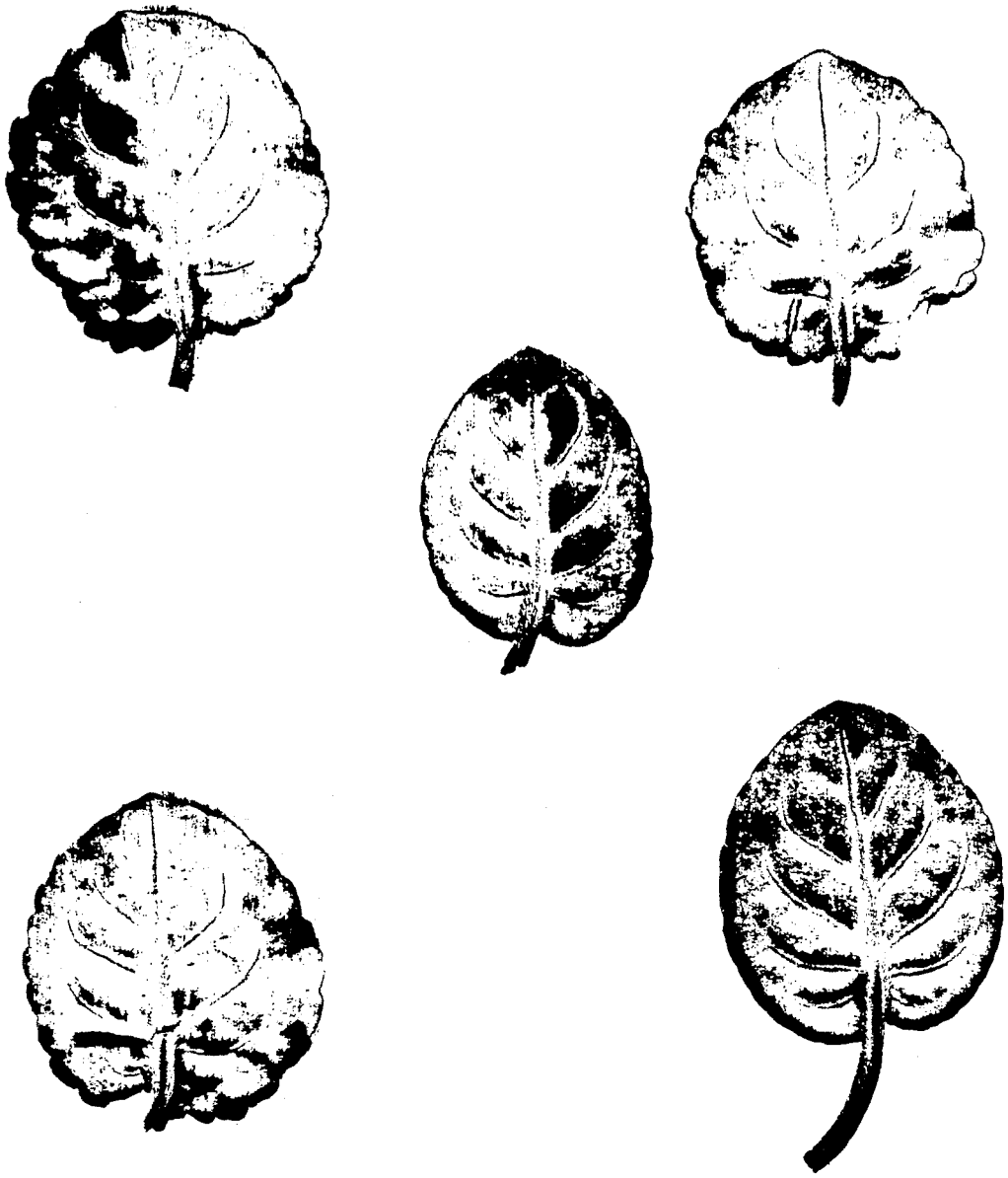

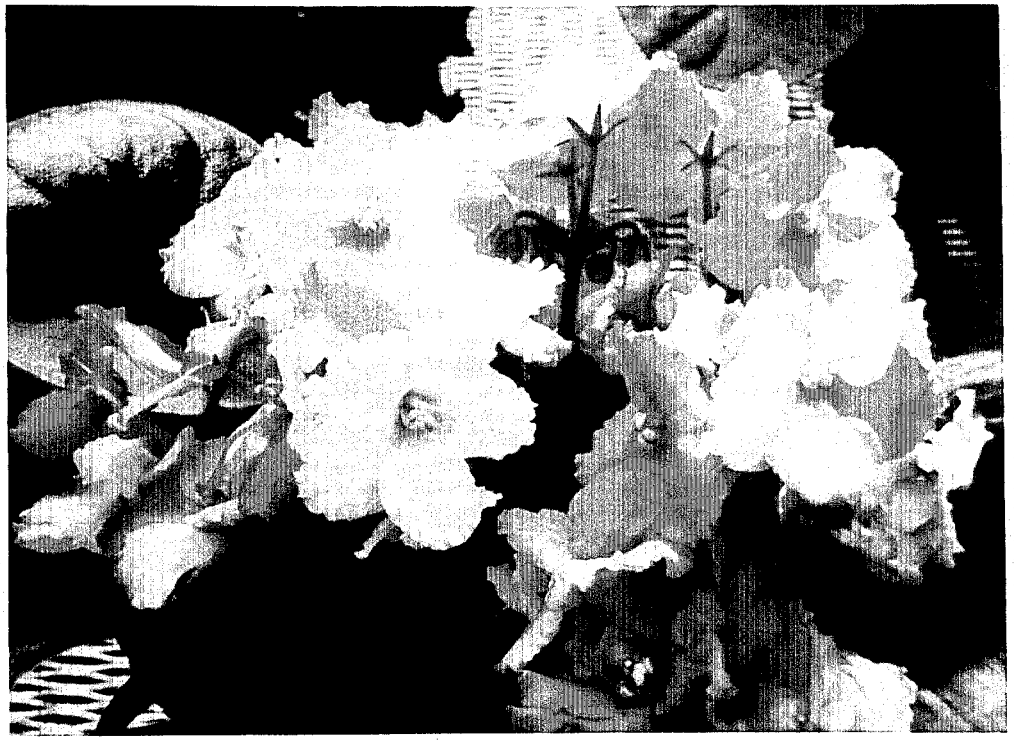
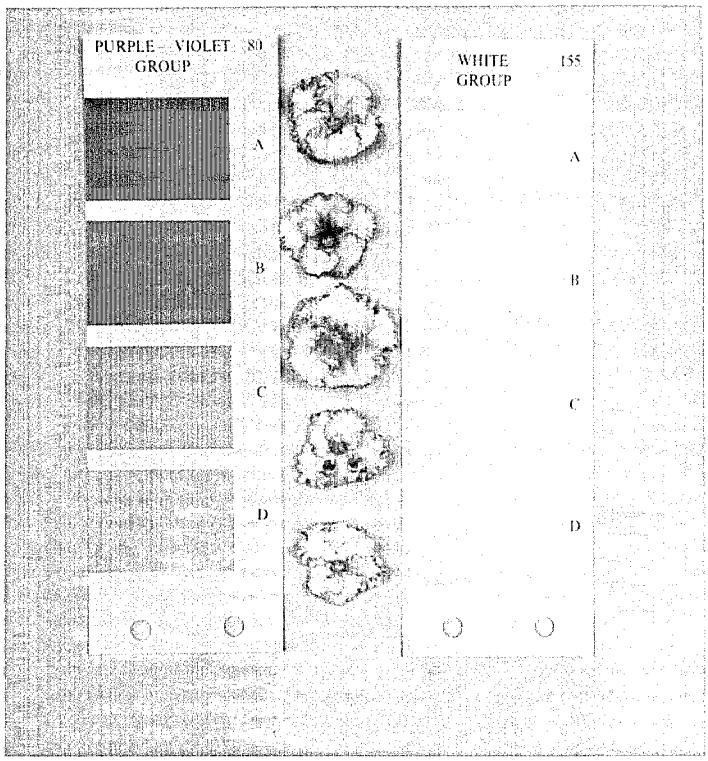
PURPLE - VIOLET GROUP
80
A
B
C
D
WHITE GROUP
155
A
B
C
D